United States Patent
Schlichting et al.

(10) Patent No.: US 12,217,864 B2
(45) Date of Patent: Feb. 4, 2025

(54) SYSTEM, MEDICAL DEVICES, NETWORK COMPONENTS, DEVICES, PROCESSES AND COMPUTER PROGRAMS FOR MEDICAL DEVICES AND FOR NETWORK COMPONENTS

(71) Applicant: Drägerwerk AG & Co. KGaA, Lübeck (DE)

(72) Inventors: Stefan Schlichting, Lübeck (DE); Simon Gisch, Lübeck (DE); Tobias Klotz, Lübeck (DE)

(73) Assignee: DRÄGERWERK AG & CO. KGAA, Lübeck (DE)

(*) Notice: Subject to any disclaimer, the term of this patent is extended or adjusted under 35 U.S.C. 154(b) by 272 days.

(21) Appl. No.: 17/229,150

(22) Filed: Apr. 13, 2021

(65) Prior Publication Data

US 2021/0319896 A1     Oct. 14, 2021

(30) Foreign Application Priority Data

Apr. 14, 2020   (DE) ...................... 10 2020 002 264.2

(51) Int. Cl.
*G16H 40/67* (2018.01)
*G06F 21/10* (2013.01)
*G06F 21/12* (2013.01)

(52) U.S. Cl.
CPC ............. *G16H 40/67* (2018.01); *G06F 21/10* (2013.01); *G06F 21/125* (2013.01)

(58) Field of Classification Search
None
See application file for complete search history.

(56) References Cited

U.S. PATENT DOCUMENTS

| 7,143,297 B2 | 11/2006 | Buchheit et al. |
| 2005/0289072 A1* | 12/2005 | Sabharwal ............ G06F 21/121 705/59 |
| 2009/0055320 A1* | 2/2009 | Goertler ............. G06Q 20/1235 705/59 |

(Continued)

FOREIGN PATENT DOCUMENTS

| WO | WO-2010009896 A1 * | 1/2010 | ............. G06F 21/10 |
| WO | WO-2020077452 A1 * | 4/2020 | ............. G16H 20/10 |

OTHER PUBLICATIONS

Cabeleira, M. T., "Medical Systems Integration", ProQuest Dissertations & Theses. (2014) (Year: 2014).*

*Primary Examiner* — Clay C Lee
(74) *Attorney, Agent, or Firm* — McGlew and Tuttle, P.C.

(57) ABSTRACT

A system, medical devices, network components, devices, processes and computer programs for medical devices and for network components are provided. The process (10) for a first medical device (400; 400b) for the use of a license-based system function of a network component (500) in a network (600) includes a transmission (11) of a request for an available license into the network (600) and a reception (12) of a reply from a second medical device. The reply indicates that a license for the system function is available at the second medical device. The process includes a request (13) for the available license from the second medical device and reception (14) of information on the available license from the second medical device. The process provides the system function based on the information on the license from the second medical device (400; 400a).

18 Claims, 5 Drawing Sheets

(56) References Cited

U.S. PATENT DOCUMENTS

| | | | |
|---|---|---|---|
| 2014/0283011 A1* | 9/2014 | Orona | G16H 20/17 |
| | | | 726/18 |
| 2015/0058229 A1* | 2/2015 | Wiacek | G06Q 50/184 |
| | | | 705/310 |
| 2017/0116694 A1 | 4/2017 | Gabie et al. | |
| 2017/0302657 A1* | 10/2017 | Moskal | G06F 21/44 |
| 2018/0247353 A1* | 8/2018 | Al-Ali | A61B 5/0205 |
| 2019/0108902 A1 | 4/2019 | Parthan et al. | |
| 2020/0242214 A1* | 7/2020 | Radian | G06F 21/125 |

* cited by examiner

SYSTEM, MEDICAL DEVICES, NETWORK COMPONENTS, DEVICES, PROCESSES AND COMPUTER PROGRAMS FOR MEDICAL DEVICES AND FOR NETWORK COMPONENTS

CROSS REFERENCE TO RELATED APPLICATIONS

This application claims the benefit of priority under 35 U.S.C. § 119 of German Application 10 2020 002 264.2, filed Apr. 14, 2020, the entire contents of which are incorporated herein by reference.

TECHNICAL FIELD

The present invention pertains to a system, to medical devices, to network components, to devices, to processes and to computer programs for medical devices and for network components, especially but not exclusively to a concept for distributing licenses for system functions in a network having medical devices.

TECHNICAL BACKGROUND

The networking of medical devices plays an ever-increasing role in clinical settings. Thus, many different medical devices are now used in patient monitoring. Examples of such medical devices are devices for monitoring vital parameters, for example, pulse, blood pressure, oxygen saturation, hemodynamic monitoring, ventilators, devices for monitoring a gas concentration in the breath of the patient, devices for administering drugs, etc. These devices are increasingly networked with one another, so that detected information can be exchanged and analyzed between the devices.

Distributed systems of electromedical devices and clinical IT systems (information technology systems) at clinical workstations have been of ever-increasing significance, because it is expected that an added value can be obtained in the treatment or monitoring of patients from an integration at the data and function level. Electromedical devices and clinical software systems are called components of such systems. Components that offer a system function, which is embodied on the basis of other participants in the distributed system and is activated by a license, typically also exist in these distributed systems.

A classical licensing system is described, for example, in the document U.S. Pat. No. 7,143,297 B2. A process for protecting computer software and/or computer-readable data against unauthorized use is described here. A coding of the software is carried out by the licensor as a function of license parameters, and the software is stored on the premises of the licensee. License parameters can then be transmitted by the licensor to the licensee in a coded form and an automatic decoding of the software can then be carried out as a function of the stored license parameters during the use of the software by the licensee. The coding of the software is initialized as a function of a secret firm key (FK), which is selected freely by the licensor. The coding of the transmission of license parameters is carried out as a function of a secret private serial key (SK). The decoding of the software or of the data is initialized depending on the FK selected by the licensor. The process makes possible an especially secure protection against copying and makes possible the storage of a plurality of mutually independent license parameters of different licensors.

All licensees use the same licensed technology provider in such a system. This may have an adverse effect on failure safety, because there is a central licensed component, whose failure may lead to a system failure. Moreover, there also may be a license for the system function provider in such systems. This may lead to the problem that this license is exhausted in case of the purchase of new electromedical devices, i.e., if the number of allowed devices is exceeded.

The communication within a distributed system of electromedical devices and clinical IT systems can take place on the basis of IEEE 11073 SDC (Institute of Electrical and Electronics Engineers, Service Device Connectivity), which allows a secured channel between two components on the basis of a secured TLS connection (Transport Layer Security).

SUMMARY

Against this background, there is therefore a need for creating an improved concept for issuing licenses for system functions in a network with medical devices.

Exemplary embodiments are based on the core idea that medical devices in such a network scenario can share licenses for system functions among one another. Thus, a first medical device can then obtain a license from a second medical device, without a central licensor being involved.

Exemplary embodiments therefore create a process for a first medical device for using a license-based system function of a network component in a network. The process comprises a transmission of a request for an available license into the network and a reception of a reply from a second medical device, wherein the reply indicates that a license is available for the system function at the second medical device. The process further comprises a request for the available license from the second medical device and a reception of information on the available license from the second medical device. The process comprises, moreover, a use of the system function with the use of the information on the license from the second medical device. Exemplary embodiments can thus make possible a direct sharing of licenses between medical devices.

Moreover, exemplary embodiments create a process for providing a license to a first medical device from a second medical device, wherein the license authorizes the use of a license-based system function in a network component in a network. The process comprises a reception of a request for an available license from the first medical device at the second medical device and a transmission of a reply from the second medical device to the first medical device. The reply indicates that the license for the system function is available at the second medical device. The process further comprises a reception of a request for the available license at the second medical device and a provision of information on the available license by the second medical device to the first medical device.

Another exemplary embodiment is a process for a network component for providing a system function for medical devices in a network. The process comprises a use of a license for the system function for a first medical device and a provision of the system function for the first medical device based on the license. The process further comprises a reception of a request for the system function from a second medical device and a reception of information on the license from the second medical device. The process comprises, moreover, a provision of the system function for the second medical device based on the license.

Exemplary embodiments can thus make it possible to share a license for a system function between medical devices without having to resort to a central licensor.

The first medical device may be configured in some exemplary embodiments to share, in turn, the license. The process for the first medical device then further comprises a reception of a request for an available license for the system function from a third medical device and a transmission of a reply to the third medical device. The reply indicates that the license for the system function is available at the first medical device. The process comprises, moreover, a reception of a request for the available license from the third medical device and a provision of the information on the available license to the third medical device. Exemplary embodiments can thus make possible a distributed licensing mechanism.

The process may comprise, moreover, a termination of a use of the system function by the first medical device after the provision of the information on the available license to the third medical device. From the viewpoint of the network component, the process taking place there may comprise, furthermore, a termination of the provision of the system function to the first medical device prior to the provision of the system function to the second or third medical device. It can thus be ensured that the same license is not used simultaneously by a plurality of medical devices.

The use of the system function can in this case comprise a provision of the license from the medical device to the network component for checking and activating the system function. Analogously, a checking of a valid sharing of the license from the first medical device to the second medical device can take place at the network component. A controlled or monitored sharing of licenses can thus take place in exemplary embodiments.

The checking may comprise at the network component, for example, a reception of a confirmation of the sharing from the first medical device, so that the system function does not become able to be used at any other medical device as long as this has not been confirmed by a sharing medical device to the network component. The process of the network component may also comprise a refusal to provide the system function for the second medical device if the result of the checking is negative. It can thus be ensured that the system function will not be used without a license.

For example, the system function may comprise the recording of a diagnostic electrocardiogram, ECG. The system function may be able to be made usable in exemplary embodiments staggered over time by sharing licenses to a plurality of medical device, so that, for example, diagnostic ECGs can be recorded staggered over time for different patients based on the same license.

The first medical device and the second medical device may originate from different manufacturers in some exemplary embodiments. Exemplary embodiments can make it possible to share licenses regardless of the manufacturer.

For example, the information on the license may be contained in a certificate. Exemplary embodiments can thus make it possible to check the license in a simple manner.

The use of the system function may comprise the establishing of a secured communication channel between the first medical device and the network component. The secured communication channel contributes to a tamper-proof communication.

The transmission of the request for the available license into the network may comprise a transmission of a wireless message in the network. A plurality of medical devices can be reached in the network by the transmission of a wireless message and the probability of finding an available license can thus be increased.

Another exemplary embodiment is a computer program with a program code for carrying out one of the processes being described here when the program code is executed on a computer, on a processor or on a programmable hardware component. A machine-readable data storage medium with such a program code is another exemplary embodiment.

Exemplary embodiments create, moreover, a device for a medical device for the use of a system function of a network component in a network. The device comprises at least one interface, which is configured for communication in the network, and a control module, which is configured for carrying out one of the above-described processes. Another exemplary embodiment is a medical device with such a device.

Exemplary embodiments create, furthermore, a device for a network component for providing a system function for medical devices in a network. The device comprises at least one interface, which is configured for the communication in the network, and a control module, which is configured to carry out one of the above-described processes. A network component with such a device is another exemplary embodiment.

Finally, exemplary embodiments also create a system with a plurality of medical devices according to the above description and with at least one network component according to the above description.

Some examples of devices and/or processes will be explained in more detail below with reference to the attached figures.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
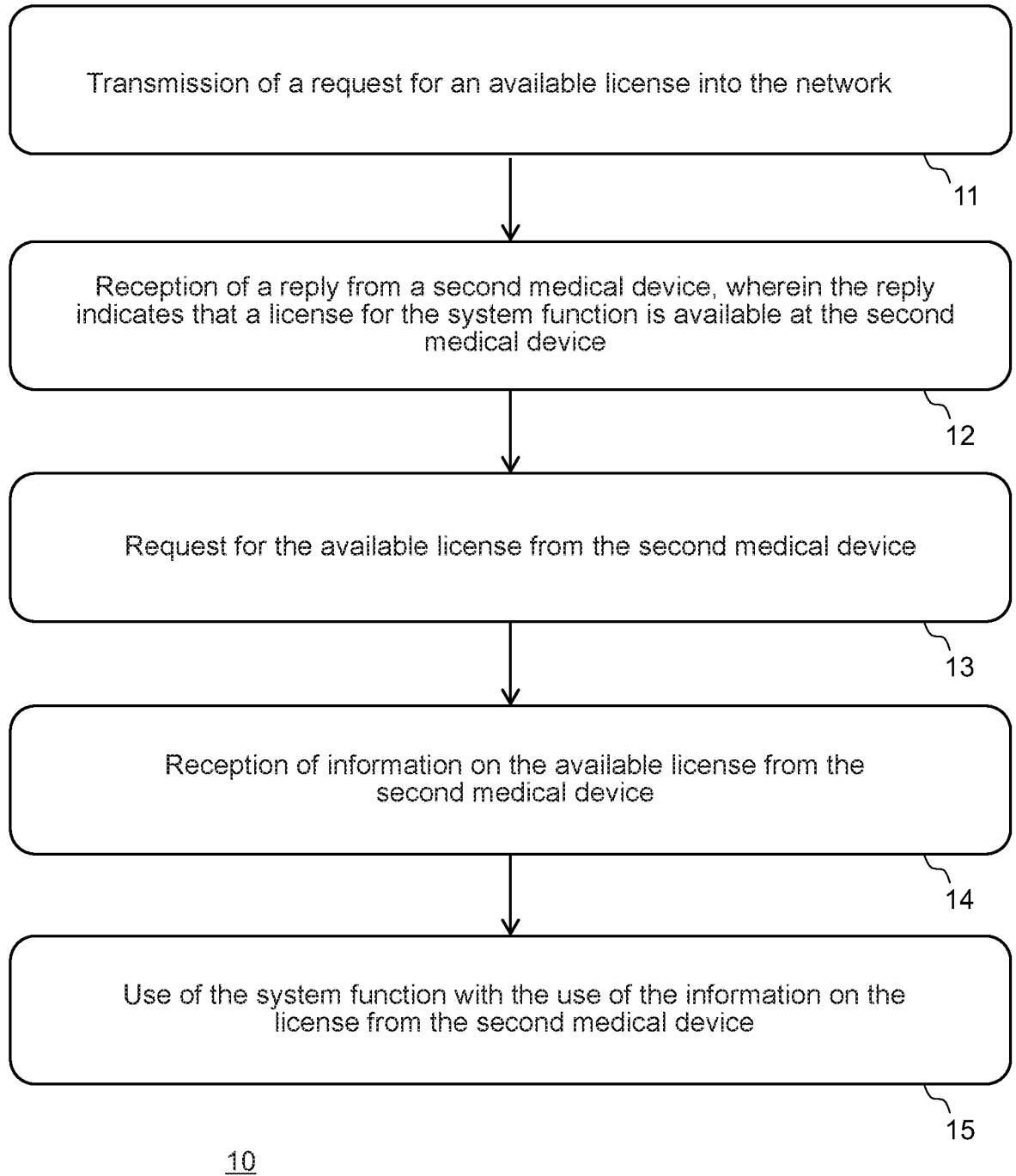
FIG. 1 is a block diagram of an exemplary embodiment of a process for a first medical device for the use of a license-based system function of a network component in a network.

Referring to the drawings, different examples will now be described in more detail with reference to the attached figures. The thicknesses of lines, layers and/or areas may be exaggerated in the Figures for the illustration.

Additional examples may cover modifications, equivalents and alternatives, which are within the scope of the disclosure. Identical or similar reference numbers pertain in the entire description of the figures to identical or similar elements, which may be implemented in a mutually identical form or in a similar form in a comparison with one another, while they provide the same function or a similar function.

It is apparent that if an element is described as being "connected" or "coupled" to another element, the elements may be connected or coupled directly or via one or more intermediate elements. If two elements A and B are combined with the use of an "or," this shall be understood to mean that all possible combinations are disclosed, i.e., only A, only B as well as A and B, unless something else is explicitly or implicitly defined. An alternative formulation for the same combinations is "at least one of A and B" or "A and/or B." The same applies, mutatis mutandis, to combinations of more than two elements.

Exemplary embodiments will be explained in more detail below. A license for using a system function, which is provided by a network component, is shared in this case from a first medical device to a second medical device. The network component, the first medical device and the second medical device are coupled in this case via a network, i.e., these can communicate with one another via the network. Typical networks, which may be configured for use for this purpose, are Internet protocol-based networks, such as LANs (Local Area Networks), WANs (Wide Area Networks), WLANs (Wireless LANs), Internet, Intranet, etc.

FIG. 1 shows a block diagram of an exemplary embodiment of a process 10 for a first medical device for the use of a license-based system function of a network component in a network. The process comprises a transmission 11 of a request for an available license into the network and a reception 12 of a reply from a second medical device. The reply indicates that a license for the system function is available at the second medical device. The process comprises, moreover, a request 13 for the available license from the second medical device and a reception 14 of information on the available license from the second medical device. The process further provides for a use 15 of the system function with the use of the information on the license from the second medical device.

The medical devices are defined as terminals in this case, which carry out certain functions at a patient or at a hospital bed. These are connected via the network to one another and also to the network component. The network component may be any desired server, access/gateway or network node, which offers the system function, e.g., a service or an access, to the medical devices. The system function is not available freely, but is subject to a permit (license) for their use.

A license is defined, in general, as a permit to use, for example, for a software, for an access or for a function. An example is the permit to use said system function, which is offered by the network component.

Figure 2:
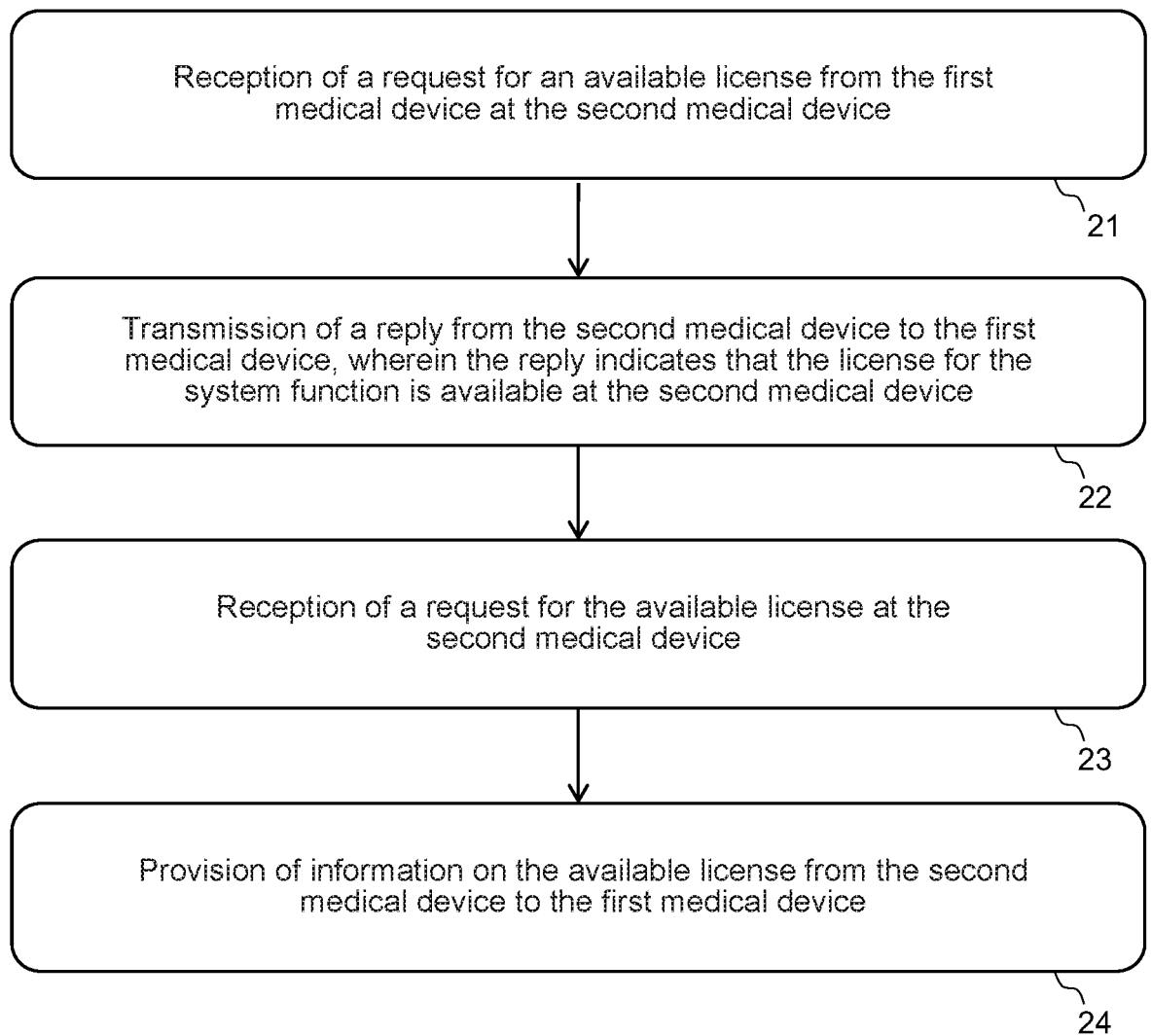
FIG. 2 is a block diagram of an exemplary embodiment of a process for providing a license to a first medical device from a second medical device.

A process is shown from the viewpoint of the second medical device in FIG. 2. FIG. 2 shows a block diagram of an exemplary embodiment of a process 20 for providing a license for a first medical device from a second medical device. The process comprises a reception 21 of a request for an available license from the first medical device at the second medical device and a transmission of a reply from the second medical device to the first medical device. The reply indicates that the license for the system function is available at the second medical device. As is also shown in FIG. 2, a reception 23 of a request for the available license at the second medical device and a provision 24 of information on the available license by the second medical device to the first medical device will follow.

Figure 3:
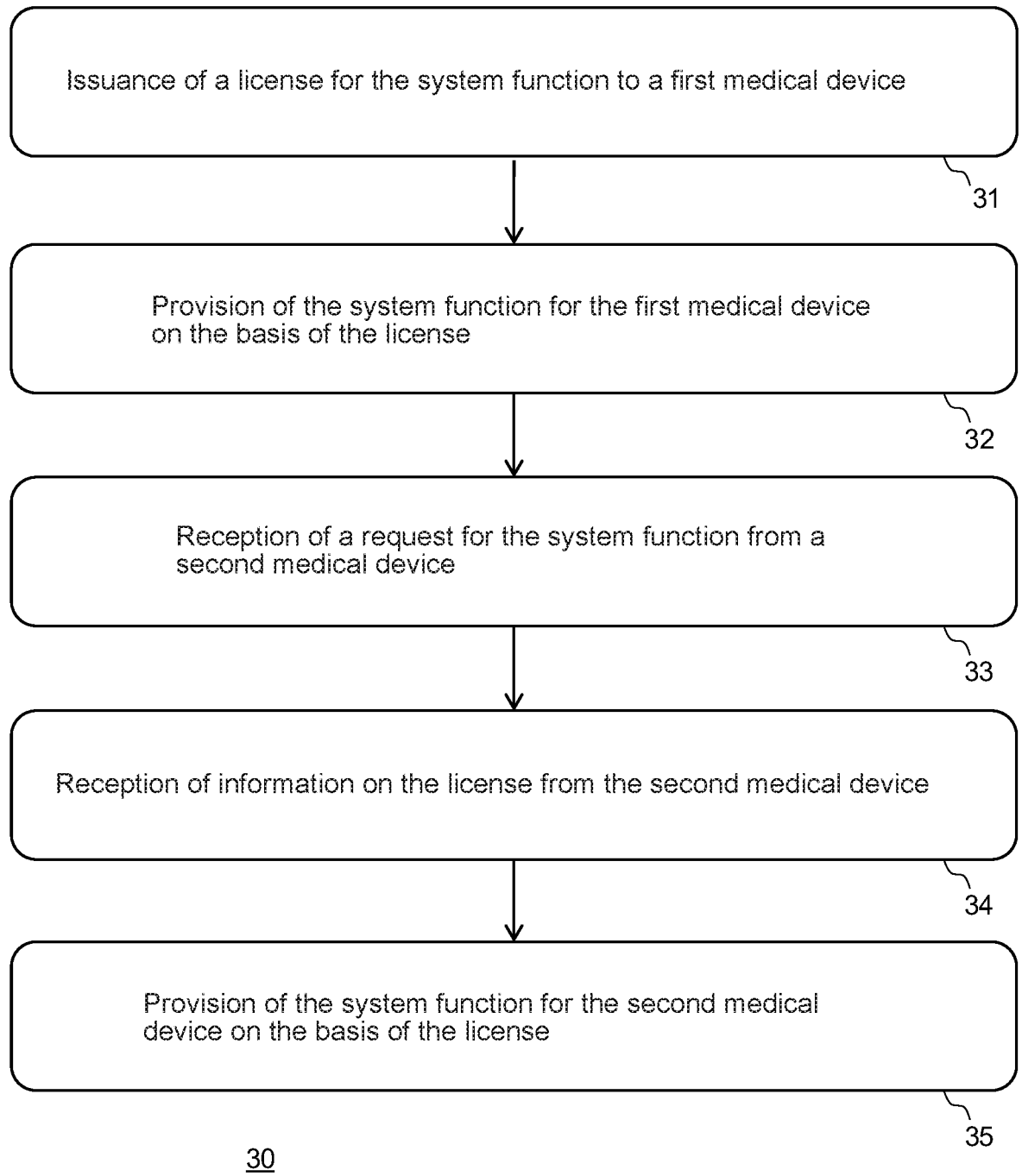
FIG. 3 is a block diagram of an exemplary embodiment of a process for a network component for providing a system function for medical devices in a network.

FIG. 3 shows a block diagram of an exemplary embodiment of a process 30 for a network component for providing a system function for medical devices in a network. The process 30 provides for a use 31 of a license for the system function for a first medical device and for a provision 32 of the system function for the first medical device based on the license. The use 31 may also comprise in some exemplary embodiments an issuance of the license. It is, however, also possible, in general, that the license was originally issued by a licensing unit, which does not correspond to the network component. The process 30 comprises, moreover, a reception 33 of a request for the system function from a second medical device and a reception 34 of information on the license from the second medical device. The process comprises, furthermore, a provision 35 of the system function for the second medical device based on the license.

In some exemplary embodiments, the license may be shared again by the first medical device. The process 10 comprises in this case a reception of a request for an available license for the system function from a third medical device and a transmission of a reply to the third medical device, wherein the reply indicates that the license for the system function is available at the first medical device. The process 10 further comprises in this case a reception of a request for the available license from the third medical device and a provision of the information on the available license to the third medical device.

Figure 4:
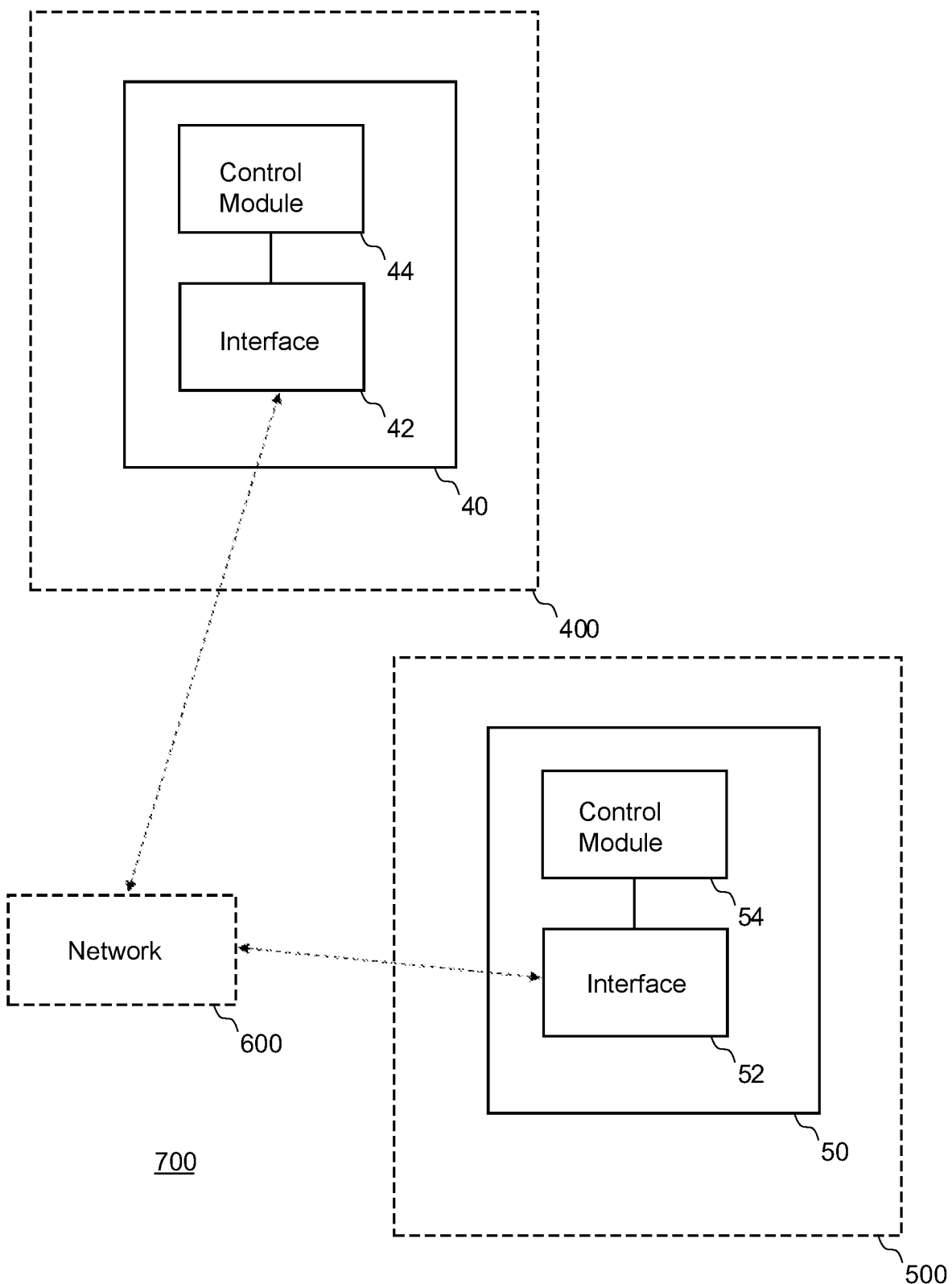
FIG. 4 is a block diagram of an exemplary embodiment of a device for a medical device, of an exemplary embodiment of a medical device, of an exemplary embodiment of a device for a network component, and of an exemplary embodiment of a network component.

FIG. 4 shows a block diagram of an exemplary embodiment of a device 40 for a medical device 400 and a block diagram of an exemplary embodiment of a medical device 400. Optional components are indicated by broken lines. FIG. 4 shows, moreover, a block diagram of an exemplary embodiment of a device 50 for a network component 500 and a block diagram of an exemplary embodiment of a network component 500.

The device 40 for the medical device 400 for using a system function of the network component 500 in a network 600 comprises an interface 42, which is configured for the communication in the network 600. The communication in the network 600 is indicated by two-ended arrows drawn in broken lines. The device 40 comprises, moreover, a control module 44, which is coupled with the interface 42 and which is configured for carrying out one of the processes 10 or 20. FIG. 4 also illustrates an exemplary embodiment of a medical device 400 with a device 40 (in a view drawn in broken lines, because it is optional from the viewpoint of the device 40).

FIG. 4 shows, moreover, an exemplary embodiment of a device 50 for a network component 500 for providing a system function for medical devices 400 in a network 600. The device 50 comprises an interface 52, which is configured for the communication in the network 600. The device 50 comprises, moreover, a control module 54, which is coupled with the interface 52, and which is configured for carrying out one of the processes 30. FIG. 4 also illustrates an exemplary embodiment of a network component 500 with the device 50 (drawn with broken lines, because it is optional from the viewpoint of the device 50).

FIG. 4 illustrates, moreover, a system 700, which may comprise a plurality of medical devices 400, and which comprises at least one network component 500.

The interfaces 42, 52 may be configured in exemplary embodiments as typical interfaces for communication in networks. For example, these may be configured in exemplary embodiments as corresponding contacts. They may also be configured in exemplary embodiments as separate hardware. They may comprise memories, which store the signals to be transmitted and/or to be received at least temporarily. The interfaces 42, 52 may be configured to receive electrical signals, for example, as a bus interface, as an optical interface, as an Ethernet interface, as a wireless interface, etc. The interfaces 42, 52 may, moreover, also be configured in exemplary embodiments for wireless transmission and comprise a radio front end as well as corresponding antennas. Further, the interfaces 42, 52 may comprise synchronization mechanisms for the one or more types of connection for the synchronization with the respective transmission medium.

The control modules 44 54 may comprise in exemplary embodiments one or more freely selectable controllers, microcontrollers, network processors, processor cores, such as Digital Signal Processor cores (DSPs), programmable hardware components, etc. Exemplary embodiments are not limited to a particular type of processor core. Any desired processor cores or even a plurality of processor cores or microcontrollers are conceivable for implementing a control module 44, 54. Implementations in an integrated form with other devices are conceivable as well, for example, in a control unit, which additionally also comprises one or more other functions. A control module 44, 54 may be embodied in exemplary embodiments by a processor core, by a computer processor core (CPU=Central Processing Unit), by a graphics processor core (GPU=Graphics Processing Unit), by an application-specific integrated circuit core (ASIC=Application-Specific Integrated Circuit), by an integrated circuit (IC=Integrated Circuit), by a one-chip system core (SOC=System on Chip), by a programmable logic element or by a field-programmable gate array with a microprocessor (FPGA=Field Programmable Gate Array) as the core of the component or of the components.

Accordingly, a licensing of system functions can take place in exemplary embodiments. A possibility of using this system function can thus be created in a distributed system of electromedical devices 400 and clinical IT systems 500. It is potentially unnecessary for all the components to have originated from one manufacturer, and it can thus also be possible that licenses are distributed to third parties, without these having to use the same licensed technology. The above-mentioned medical devices (first medical device and second medical device, FIGS. 1 and 2) may thus originate from different manufacturers.

In some exemplary embodiments, the provision or use of the system function can be terminated or stopped after the license has been shared. The process 10 will in this case comprise on the side of the sharing medical device a termination of a use of the system function by the sharing medical device after the provision of the information on the available license to another medical device receiving the license. From the viewpoint of the network component 500, the process 30 taking place there comprises, furthermore, a termination of the provision of the system function for the first (sharing) medical device prior to the provision of the system function for the second medical device (medical device receiving the license). Moreover, the process 30 may comprise a refusal to provide the system function for the second medical device on the side of the network component providing the system function if the checking shows a negative result.

A system 700 may comprise in exemplary embodiments 1 . . . n (n=positive integer) system function participants, e.g., electromedical devices (medical devices) and/or clinical IT systems (network components). The respective interfaces 42, 52 may be configured for installing a license. The devices 40, 50 may have, moreover, storage possibilities in order to store the installed licenses. The interfaces 42, 52 may, moreover, be configured to authenticate the individual components.

The use 15 of the system function may comprise a provision of the license for the network component 500 for checking and activating the system function. A checking of a valid sharing of the license from the first medical device to the second medical device can take place from the viewpoint of the network component 500. This may take place, for example, by receiving a confirmation of the sharing from the first medical device.

Another mechanism, which can be used in exemplary embodiments for the mutual authentication and verification of the license, is the use of certificates. The information on the license may be contained in a certificate. For example, a secure communication channel may be established between the individual components. Secure means in this connection that the communication channel is secured by coding. The use of the system function may comprise the establishing of a secured communication channel between the medical device 400 and the network component 500. The establishing of such a secure channel may likewise take place between medical devices for sharing the license. One possibility of achieving this is the use of TLS (Transport Layer Security) with an X.509 certificate, which points to a Trust Root. X.509 is a standard for issuing digital certificates, whose authenticity is guaranteed by a certification unit (Trust Root, trustworthy source). A coded and hence secure communication can be established in this case on the basis of one or more key pairs, a public key and a private key each.

The system shown in FIG. 4 may then also have one or more system function providers (network components) 500, e.g., a clinical IT system, but electromedical devices may offer a system function as well, and they may accordingly be network components 500. At least one system function is provided in this case, and a plurality of system functions are preferably provided, which must be activated by a license. Further examples of such a system function are report generation, the sharing of data, and the calculation of clinical parameters or diagnoses. The system function may comprise, for example, the recording of a diagnostic electrocardiogram, ECG.

The devices 40, 50 may comprise in exemplary embodiments corresponding memories for "Trust Root(s)" or certification, as well as the above-described communication interfaces 42, 52, via which authentication information and licenses can be selected. Moreover, data and/or commands can be received via the communication interfaces 42, 52 from other components or be transmitted to these.

Figure 5:
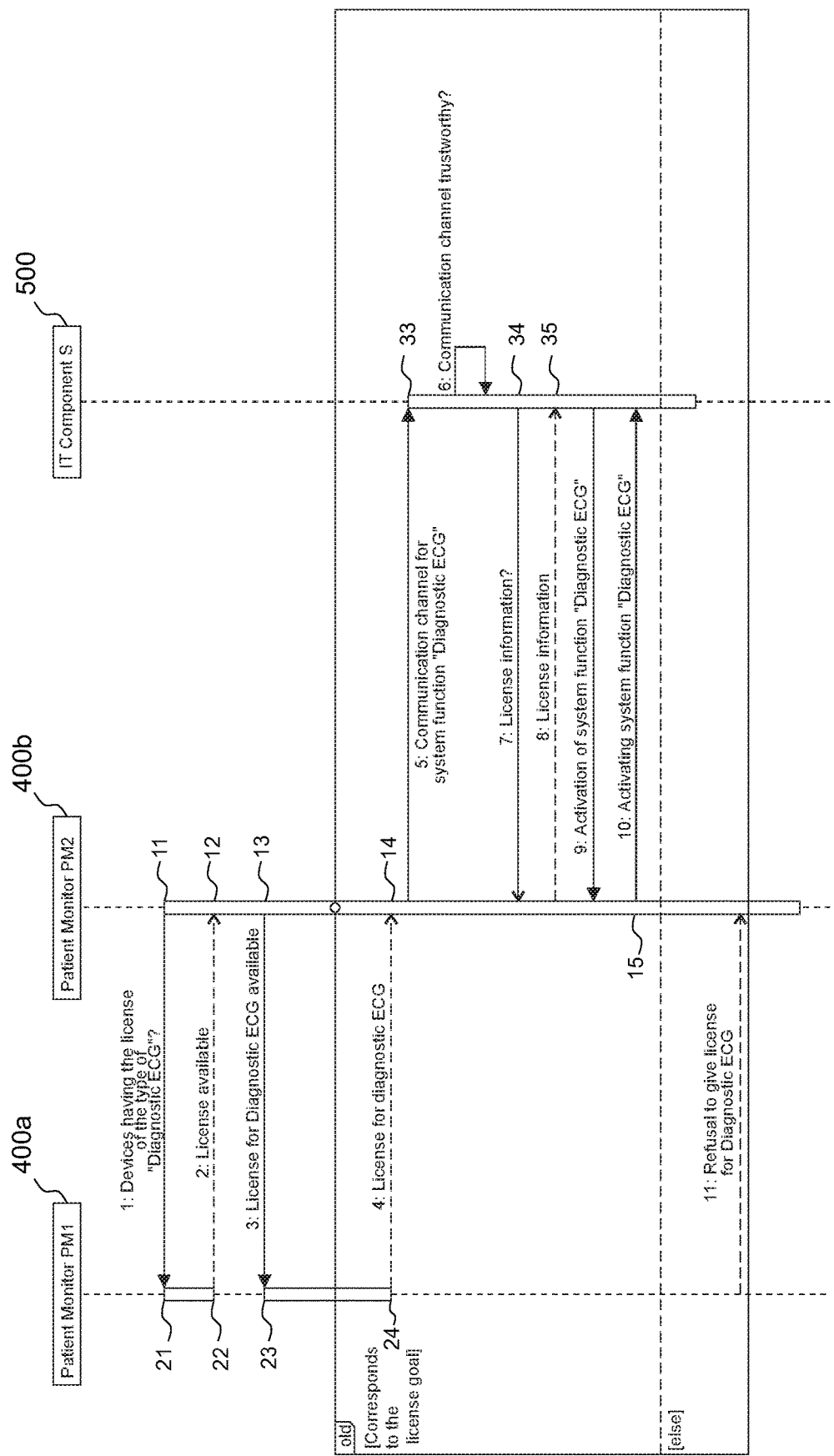
FIG. 5 is a sequence diagram in an exemplary embodiment.

FIG. 5 shows a sequence diagram in an exemplary embodiment. FIG. 5 shows two medical devices 400*a* and 400*b* (patient monitors) as well as a network component 500 (IT component). The medical device 400*b* receives in this exemplary embodiment a license for a system function (diagnostic ECG), which is offered by the IT component 500. The medical device 400*b* transmits for this a search request for devices that have a license of this type into the network. The transmission 11 of the request for the available license into the network comprises in this exemplary embodiment a transmission of a wireless message in the network.

The wireless message is received, 21, by the medical device 400*a*, after which this gives a positive reply 22 (license available) to this. The medical device 400*b* makes a concrete request 13 for the available license to the medical device 400a upon receiving 12 the reply (potentially a plurality of replies from the network). This medical device 400a receives, 23, the request and provides, 24, corresponding information on the available license for the medical device 400b. Should the license still be needed by the medical device 400a, the provision of the license may also be refused to the medical device 400b (last step in FIG. 5). After reception 14 of the information on the license, the license is used, 15, by the medical device 400b. In the exemplary embodiment according to FIG. 5, a communication channel is established at first for the request 33 for the system function "diagnostic ECG" to the network component 500 and it is checked there. The license information is then selected by the network component from the medical device 400b. In case of a valid license, the system function is then provided, 35, by the network component.

The license may have been provided before by the network component 500 to the medical device 400a. A certificate may accordingly be provided for the system function participant at a communication interface by the network component 500 or also by another licensor. Further, corresponding communication partners, which offer, for example, one or more system functions, are provided by the network.

The network component 500 or another licensor may generate in exemplary embodiments a license for the use of the at least one optional system function including license information. For example, the generated license information comprises a license code, a license goal, etc. The generated license may then be installed in the system function participant (medical device) for the use of the optional system function provided by the system function provider 500. A communication can in this case be established between the system function participant 400a, 400b and the system function provider 500, and the system function provider 500 may check authentication information for trustworthiness, for example, by an X.509 certificate chain.

The respective licenses and also communication partners may in this case be authenticated, and their public keys may be checked, for example, by certificates. Depending on the communication sequence, a certificate chain can thus be established, and the authenticity of a key can be checked with a preceding certificate. It is also possible to speak of validation or certification paths in this procedure.

A reading of license information from the system function participant 400a, 400b can then be carried out by means of a checked (secure) communication channel by the system function provider. The optional system function of the system function provider can then be activated after successful checking of the read license information. For example, the license information was checked successfully precisely when the read license information matches the optional system function.

A message, which indicates that the license is no longer available at the system function participant, can optionally be received at the network component 500 in some additional exemplary embodiments. The activation of the system function may optionally be carried out by the system function participant, or an optional activation of the function can take place for system function participants who do not have a license if a certain number of electromedical components have an active license.

For example, 10 devices 400 are purchased from a manufacturer in another exemplary embodiment, and the manufacturer has also sold the system function provider 500. Additional devices 400 were purchased from third parties and from the first manufacturer. If the number of active licenses exceeds 12, the function is activated for 6 devices from third parties. Licenses can be automatically exchanged between the electromedical devices 400 in exemplary embodiments. A license may be bound to a certificate and is thus automatically bound to one end point and to one time interval. In some exemplary embodiments, the licenses are not licenses that activate a function on the electromedical device, but they do so at the system function provider. Moreover, a license can only be shared to a communication partner if this is trustworthy. Different types of licenses are, for example, tokens, BoundToEndpoint, Floating, etc.

For example, 10 patient monitors 400 from company A have a license each at a gateway G 500 from company A. The gateway G 500 also allows the export of the data for devices from a third company B in this case.

A patient monitor PM1 400a has a license for the determination of diagnostic ECG. The diagnostic ECG will be determined by a clinical IT component S 500. A second patient monitor PM2 400b has at first no license for the determination of diagnostic ECG. Instead of replacing the device 400b at the patient, the patient monitor PM2 400b searches for devices, for example, by means of wireless message in the network, which have a license of a defined type, and takes over this floating license in the network. It can then activate the clinical component S 500.

A patient monitor PM1 400b may refuse to provide the licenses used for a communication partner, e.g., if this does not correspond to the license goal indicated, cf. last step in FIG. 5.

The information can be generated, exchanged and checked independently from a defined license technology due to the certificates. The certificate chain can be checked instead of a proprietary format. A markedly increased failure safety may be achieved due to the elimination of a central component.

Exemplary embodiments may be, for example, a computer program with a program code for carrying out one or more of the above processes, or the exemplary embodiments may refer to these if the computer program is executed on a computer or processor. Steps, operations or processes of different, above-described processes may be carried out by programmed computers or processors. Examples may also cover program storage devices, e.g., digital data storage media, which are machine-, processor- or computer-readable and code machine-executable, processor-executable or computer-executable programs of instructions. The instructions execute some or all of the steps of the above-described processes or cause these to be executed. The program storage devices may comprise or be, e.g., digital memories, magnetic storage media, for example, magnetic disks and magnetic tapes, hard drives or optically readable digital storage media. Additional examples may also cover computers, processors or control units, which are programmed to execute the steps of the above-described processes, or (field)-programmable logic arrays ((F)PLAs=(Field) Programmable Logic Arrays) or (field)-programmable gate arrays ((F)PGA=(Field) Programmable Gate Arrays), which are programmed to execute the steps of the above-described processes.

Functions of different elements shown in the figures as well as the function blocks indicated may be implemented in the form of dedicated hardware, e.g., of "a signal provider," "of a signal processor unit," "of a processor," "of a control," etc., as well as as hardware capable of executing software in conjunction with corresponding software. In case of provision by a processor, the functions may be provided by an individual dedicated processor, by an individual, jointly used processor or by a plurality of individual processors, some of which or all of which may be used together. However, the term "processor" or "control" is not limited exclusively to hardware exclusively capable of executing software, but it may comprise digital signal processor hardware (DSP hardware; DSP=Digital Signal Processor), network processor, application-specific integrated circuit (ASIC=Application Specific Integrated Circuit), field-programmable logic array (FPGA=Field Programmable Gate Array), read-only memory (ROM=Read Only Memory) for storing software, random excess memory (RAM=Random Access Memory) and nonvolatile storage device (storage). Other hardware, conventional and/or customer-specific, may be included as well.

A block diagram may represent, for example, a general circuit diagram, which implements the principles of the disclosure. Similarly, a flow chart, a state transition diagram, a pseudocode and other similar processes may represent operations or steps, which are represented, for example, essentially in a computer-readable medium and are thus executed by a computer or processor, regardless of whether such a computer or processor is explicitly shown. Processes disclosed in the description or in the patent claims may be implemented by a component, which has means for executing each of the respective steps of these processes.

It is apparent that the disclosure of a plurality of steps, processes, operations or functions disclosed in the description or in the claims shall not be interpreted such that these are located in the defined order, unless this is explicitly or implicitly indicated otherwise, e.g., for technical reasons. Therefore, these are not limited to a defined order by the disclosure of a plurality of steps or functions, unless these steps or functions are not interchangeable for technical reasons. Further, an individual step, function, process or operation may include in some examples a plurality of partial steps, partial functions, partial processes or partial operations and/or may be divided into these. Such partial steps may be included and be a part of the disclosure of this individual step, unless they are explicitly ruled out.

While specific embodiments of the invention have been shown and described in detail to illustrate the application of the principles of the invention, it will be understood that the invention may be embodied otherwise without departing from such principles.

LIST OF REFERENCE NUMBERS

10 Process for a first medical device for the use of a license-based system function of a network component in a network
11 Transmission of a request for an available license into the network
12 Reception of a reply from a second medical device, wherein the reply indicates that a license for the system function is available at the second medical device
13 Request for the available license from the second medical device
14 Reception of information on the available license from the second medical device
15 Use of the system function with the use of the information on the license from the second medical device
20 Process for providing a license to a first medical device from a second medical device, wherein the license authorizes the use of a license-based system function for a network component in a network
21 Reception of a request for an available license from the first medical device at the second medical device
22 Transmission of a reply from the second medical device to the first medical device, wherein the reply indicates that the license is available for the system function at the second medical device
23 Reception of a request for the available license at the second medical device
24 Provision of information on the available license by the second medical device to the first medical device
30 Process for a network component for providing a system function for medical devices in a network
31 Use of a license for the system function for a first medical device
32 Provision of the system function for the first medical device based on the license
33 Reception of a request for the system function from a second medical device
34 Reception of information on the license from the second medical device
35 Provision of the system function for the second medical device based on the license
40 Device for a medical device for the use of a system function of a network component in a network
42 Interface
44 Control module
50 Device for a network component for the provision of a system function for medical devices in a network
52 Interface
54 Control module
400 Medical device
400a Medical device
400b Medical device
500 Network component
600 network
700 System

What is claimed is:

1. A method for a first medical device and a second device for using a license-based system function of a network component in a network, the method comprising:
transmitting a request via the first medical device for an available license into the network, the first medical device not being a central licensor;
providing the second medical device configured to carry out one or more second medical device patient monitoring functions for a patient, the second medical device receiving the request, the second medical device generating a reply as output, the second medical device not being a central licensor;
transmitting the reply from the second medical device to the first medical device without involving the central licensor, wherein the reply indicates that a license for the system function is available at the second medical device;
requesting the available license at the second medical device;
establishing a secured communication channel between the first medical device and the second medical device;
transmitting information on the available license from the second medical device to the first medical device through the secured communication channel without involving the central licensor; and
carrying out, by the first medical device, one or more first medical device patient monitoring functions at the patient or another patient by using the system function via the first medical device with a use of information of the license from the second medical device after the information of the license is transmitted to the first medical device, the first medical device not being a central licensor.

2. A process in accordance with claim 1, further comprising:
receiving a request for an available license for the system function from a third medical device;
transmitting a reply to the third medical device, wherein the reply indicates that the license for the system function is available at the first medical device;
receiving a request for the available license from the third medical device; and
providing the information on the available license to the third medical device.

3. A process in accordance with claim 2, further comprising terminating using the system function by the first medical device after providing the information on the available license to the third medical device.

4. A process in accordance with claim 1, wherein the use of the system function comprises providing the license to the network component for checking and activating the system function.

5. A process in accordance with claim 1, wherein the information on the license is contained in a certificate.

6. A process in accordance with claim 1, wherein the transmission of the request for the available license into the network comprises transmitting a wireless message to the network.

7. A process in accordance with claim 1, further comprising providing a program with a program code for executing one or more of the steps on a computer, on a processor or on a programmable hardware component.

8. A method for providing a license to a first medical device from a second medical device, wherein the license authorizes the use of a license-based system function of a network component in a network, the method comprising:
receiving a request for an available license from the first medical device at the second medical device, each of the first medical device and the second medical device being configured to carry out a medical device function for a patient, each of the first medical device and the second medical device not being a central licensor;
transmitting a reply from the second medical device to the first medical device without involving the central licensor, wherein the reply indicates that the license for the system function is available at the second medical device;
receiving a request for the available license at the second medical device;
establishing a secured communication channel between the first medical device and the second medical device;
providing information on the available license from the second medical device to the first medical device through the secured communication channel without involving the central licensor; and
carrying out, by the first medical device, the medical device function for the patient based on the license-based system function and the license after the information of the license is transmitted to the first medical device, the medical device function including monitoring one or more parameters of the patient.

9. A process in accordance with claim 8, further comprising providing a program with a program code for executing one or more of the steps on a computer, on a processor or on a programmable hardware component.

10. A method for a network component for providing a system function for medical devices in a network, the method comprising:
using a license for the system function for a first medical device to carry out a first medical device function for a patient, the medical device function including monitoring parameters of the patient;
providing the system function for the first medical device based on the license, the first medical device not being a central licensor;
receiving a request for the system function from a second medical device without involving the central licensor, the second medical device not being a central licensor;
establishing a secured communication channel between the first medical device and the second medical device;
receiving information on the license at the first medical device from the second medical device through the secured communication channel; and
providing the system function for the second medical device based on the license; and
carrying out, by the second medical device, a second medical device function for the patient or another patient by using the system function after the information of the license is received by the second medical device, the medical device function including monitoring one or more parameters of the patient.

11. A process in accordance with claim 10, further comprising terminating the provision of the system function for the first medical device prior to providing the system function to the second medical device.

12. A process in accordance with claim 10, further comprising checking for a valid sharing of the license from the first medical device to the second medical device.

13. A process in accordance with claim 10, further comprising providing a program with a program code for executing one or more of the steps on a computer, on a processor or on a programmable hardware component.

14. A device for a medical device for use of a system function of a network component in a network, the device comprising:
an interface configured to communicate via the network; and
one or more processors coupled with the interface and configured to execute one of:
a process for a first medical device for using a license-based system function of a network component in a network, the process comprising the steps of:
transmitting a request for an available license into the network;
receiving a reply at the first medical device from a second medical device, wherein the reply indicates that a license for the system function is available at the second medical device, each of the first medical device and the second medical device not being a central licensor;
requesting the available license at the second medical device;
establishing a secured communication channel between the first medical device and the second medical device;
receiving information on the available license from the second medical device through the secured communication channel; and
monitoring, by the first medical device, a patient via the system function by using the system function via the first medical device with a use of information of the license from the second medical device after the information of the license is received by the first medical device; and a process for providing the license to a first medical device from a second medical device, wherein the license authorizes the use of a license-based system function of a network component in a network, the process comprising the steps of:
receiving a request for an available license from the first medical device at the second medical device without involving the central licensor;
transmitting a reply from the second medical device to the first medical device without involving the central licensor, wherein the reply indicates that the license for the system function is available at the second medical device;
receiving a request for the available license at the second medical device without involving the central licensor;
establishing a secured communication channel between the first medical device and the second medical device; and
providing information on the available license from the second medical device to the first medical device through the secured communication channel.

15. A device in accordance with claim 14, wherein the device is a part of the medical device.

16. A device for a network component for providing a system function for medical devices in a network, the device comprising:
an interface configured for communication via the network; and
one or more processors coupled with the interface and configured to provide a license to a first medical device from a second medical device, each of the first medical device and the second medical device not being a central licensor, wherein the license authorizes the use of a license-based system function of a network component in a network, wherein providing the license comprises:
receiving a request for an available license from the first medical device at the second medical device without involving the central licensor;
transmitting a reply from the second medical device to the first medical device without involving the central licensor, wherein the reply indicates that the license for the system function is available at the second medical device;
receiving a request for the available license at the second medical device without involving the central licensor;
establishing a secured communication channel between the first medical device and the second medical device;
providing information on the available license from the second medical device to the first medical device through the secured communication channel; and
carrying out, by the first medical device, monitoring one or more parameters of a patient based on the license-based system function after the information of the available license is provided to the first medical device.

17. A device according to claim 16, wherein the device is a part of the network component.

18. A system comprising:
a plurality of medical devices, comprising a first medical device and a second medical device, for use of a system function of a network component in a network for carrying out at least one medical device function for a patient, each of the medical devices comprising a device comprising:
an interface configured to communicate via the network; and
one or more processors coupled with the interface and configured to execute one of:
a process for the first medical device for using a license-based system function of a network component in a network, the first medical device not being a central licensor, the process comprising the steps of:
transmitting a request for an available license into the network without involving the central licensor;
receiving a reply at the first medical device from the second medical device without involving the central licensor, the second medical device not being a central licensor, wherein the reply indicates that a license for the system function is available at the second medical device;
requesting the available license at the second medical device without involving the central licensor;
establishing a secured communication channel between the first medical device and the second medical device;
receiving information on the available license from the second medical device without involving the central licensor through the secured communication channel; and
using the system function with a use of information of the license from the second medical device; and
a process for providing a license to the first medical device from the second medical device, wherein the license authorizes the use of a license-based system function of a network component in a network, the process comprising the steps of:
receiving a request for an available license from the first medical device at the second medical device without involving the central licensor;
transmitting a reply from the second medical device to the first medical device without involving the central licensor, wherein the reply indicates that the license for the system function is available at the second medical device;
receiving a request for the available license at the second medical device without involving the central licensor; and
providing information on the available license from the second medical device to the first medical device without involving the central licensor;
at least one network component for providing a system function for the medical devices in a network, the network component comprising a device comprising:
an interface configured for communication via the network; and
one or more processors coupled with the interface and configured to provide a license to the first medical device from the second medical device, wherein the license authorizes the use of a license-based system function of a network component in a network, wherein providing the license comprises:
receiving a request for an available license from the first medical device at the second medical device;
transmitting a reply from the second medical device to the first medical device, wherein the reply indicates that the license for the system function is available at the second medical device;

receiving a request for the available license at the second medical device;

establishing a secured communication channel between the first medical device and the second medical device;

providing information on the available license from the second medical device to the first medical device through the secured communication channel; and carrying out, by the first medical device, the license-based system function based on the license, the license-based system function including monitoring one or more parameters of the patient.

* * * * *